(12) United States Patent
Schweinfest et al.

(10) Patent No.: US 6,210,887 B1
(45) Date of Patent: *Apr. 3, 2001

(54) METHODS FOR EVALUATING COLON TISSUE FOR EXPRESSION OF THE DRA (DOWN REGULATED IN ADENOMA) GENE

(75) Inventors: Clifford W. Schweinfest, Hampstead; Takis S. Papas, Potomac, both of MD (US)

(73) Assignee: The United States of America as represented by the Department of Health and Human Services, Washington, DC (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/184,937

(22) Filed: Nov. 2, 1998

Related U.S. Application Data

(62) Division of application No. 08/711,928, filed on Sep. 11, 1996, now Pat. No. 5,831,015, which is a division of application No. 08/424,567, filed on Apr. 17, 1995, now Pat. No. 5,569,755, which is a continuation of application No. 08/026,045, filed on Mar. 5, 1993, now abandoned.

(51) Int. Cl.[7] .............................. C12Q 1/68; C07H 21/02; C07H 21/04

(52) U.S. Cl. ........................... 435/6; 536/23.1; 536/23.5; 536/24.31

(58) Field of Search ................................ 435/6; 536/23.1, 536/23.5, 24.31

(56) References Cited

U.S. PATENT DOCUMENTS 5,650,281 * 7/1997 Vogelstein .................................. 435/6

OTHER PUBLICATIONS

Hamilton, S.R. Journal of Cellular Biochemistry, Supplement 16G:41–46, 1992.*
Goelz et al., "Hypomethylation of DNA from Benign and Malignant Human Colon Neoplasms," *Science*, vol. 228, pp. 187–190 (Apr. 1985).
Erisman et al., "Deregulation of c–myc Gene Expression in Human Colon Carcinoma Is Not Accompanied by Ampification or Rearrangement of the Gene," *Mol. Cell. Biol.*, vol. 5, No. 8, pp. 1969–1976 (Aug. 1985).
Forrester et al., "Detection of High Incidence of K–ras Oncogenes during Human Colon Tumorigenesis," *Nature*, vol. 327, pp. 298–303 (May 1987).
Feinberg et al., "Reduced Genomic 5–Methylcytosine Content in Human Colonic Neoplasia," *Cancer Research*, vol. 48, pp. 1159–1161 (Mar. 1988).

Imaseki et al., "Expression of c–myc Oncogene in Colorectal Polyps as a Biological Marker for Monitoring Malignant Potential," *Cancer*, vol. 64, pp. 704–709 (1989).
Finley et al., "Expression of myc Gene Family in Different Stages of Human Colorectal Cancer," *Oncogene*, vol. 4, pp. 963–971 (1989).
Burmer et al., "Mutations in the KRAS2 Oncogene during Progressive Stages of Human Colon Carcinoma," *Proc. Natl. Acad. Sci USA*, vol. 86, pp. 2403–2407 (Apr. 1989).
Baker et al., "Chromosome 17 Deletions and p53 Gene Mutation in Colorectal Carcinomas," *Science*, vol. 244, pp. 217–221 (Apr. 1989).
Nigro et al., "Mutations in the p53 Gene Occur in Diverse Human Tumour Types," *Nature*, vol. 342, pp. 705–708 (Dec. 1989).
Paraskeva et al., "Colorectal Carcinogenesis: Sequential Steps in the in Vitro Immortalization and Transformatioin of Human Colonic Epithelial Cells (Review)," *Anticancer Research*, vol. 10, pp. 1189–1200 (1990).
Schweinfest et al., "Subtraction Hybridization cDNA Libraries from Colon Carcinoma and Hepatic Cancer," *Genet Annal Techn Appl*, vol. 7, pp. 64–70 (1990).
Fearon et al., "Identification of a Chromosome 18q Gene That Is Altered in Colorectal Cancers," *Science*, vol. 247, pp. 49–56 (Jan. 1990).
Fearon et al., "A Genetic Model for Colorectal Tumorigenesis," *Cell*, vol. 61, pp. 759–767 (Jun. 1990).
Baker et al., "Suppression of Human Colorectal Carcinoma Cell Growth by Wild–Type p53," *Science*, vol. 249, pp. 912–915 (Aug. 1990).
Rau et al., "Chromosome and Oncogene Studies in Human Rectal and Colon Carcinomas," *Anticancer Research*, vol. 11, pp. 1477–1484 (1991).
Kinzler et al., "Identification of a Gene Located at Chromosome 5q21 That is Mutated in Colorectal Cancers," *Science*, vol. 251, pp. 1366–1370 (Mar. 1991).
Lee et al., "Positive Selection of Candidate Tumor–Suppressor Genes by Subtractive Hybridization," *Proc. Natl. Acad. Sci. USA*, vol. 88, pp. 2825–2829 (Apr. 1991).
Augenlicht et al., "Patterns of Gene Expression That Characterize the Colonic Mucosa in Patients at Genetic Risk for Colonic Cancer," *Proc. Natl. Acad. Sci. USA*, vol. 88, pp. 3286–3289 (Apr. 1991).

(List continued on next page.)

*Primary Examiner*—Carla J. Myers
*Assistant Examiner*—Diana Johannsen
(74) *Attorney, Agent, or Firm*—Fish & Richardson P.C.

(57) ABSTRACT

A new down-regulated gene called DRA, for down regulated in adenoma, maps to chromosome 7 and is believed to encode a tumor suppressor. The DRA gene encodes a highly hydrophobic protein with charged clusters located primarily in the carboxyl terminus. Additionally, the expression of the mRNA product appears to be strictly limited to the mucosa of normal colon and it is down-regulated early in colon tumorigenesis. Absence of the DRA polypeptide in tissue that usually expresses it can be used as an indicator of tissue abnormality. The DRA gene and cDNA may also have therapeutic capabilities as well.

15 Claims, 10 Drawing Sheets

OTHER PUBLICATIONS

El–Deiry et al., "High Expression of the DNA Methyltransferase Gene Characterizes Human Neoplastic Cells and Progression Stages of Colon Cancer," *Proc. Natl. Acad. Sci. USA*, vol. 88, pp. 3470–3474 (Apr. 1991).

Gorden et al., "Identification and Characterization of the Familial Adenomatous Polyposis Coli Gene," *Cell*, vol. 66, pp. 589–600 (Aug. 1991).

Kinzler et al., "Identification of FAP Locus Genes from Chromosome 5q21," *Science*, vol. 253, pp. 661–665 (Aug. 1991).

Nishisho et al., "Mutations of Chromosome 5q21 Genes in FAP and Colorectal Cancer Patients," *Science*, vol. 253, pp. 665–669 (Aug. 1991).

Schweinfest et al., "Subtraction Hybridization: An Approach to the Isolation of Genes Differentially Expressed in Cancer and Other Biological Systems (Review)," *Int'l. J. of Oncology*, vol. 1, pp. 499–506 (1992).

Rodriguez–Alfageme et al., "Suppression of Deregulated c–MYC Expression in Human Colon Carcinoma Cells ov Chromosome 5 Transfer," *Proc. Natl. Acad. Sci. USA*, vol. 89, pp. 1482–1486 (Feb. 1992).

Goyette et al., "Progression of Colorectal Cancer Is Associated with Multiple Tumor Suppressor Gene Defects but Inhibition of Tumorigenicity Is Accomplished by Correction of Any Single Defect via Chromosome Transfer," *Mol. Cell. Biol.*, vol. 12, No. 3, pp. 1387–1395 (Mar. 1992).

Culver et al., "In Vivo Gene Transfer with Retroviral Vector–Producer Cells for Treatment of Experimental Brain Tumors," *Science*, vol. 256, pp. 1550–1552, 1513 (Jun. 1992).

Nakano et al., Euro. J. Biochem., vol. 224, (1994), pp. 179–189.

Kondoh et al., "Differ. Expres. S19 Ribosomal Protein, Laminin–Binding Protein, Human Lymphocyte Antigen Class I Messenger RNAs Asso. w/Colon Carcinoma Prog. Differ.", Cancer Res., vol. 52, (1992), pp. 791–796.

Schweinfest et al., Proc. Nat'l. Acad. Sci., USA vol. 90, pp. 4166–4170 (May 1993).

Day et al., "How to Write and Publish A Scientific Paper", Second Edition, ISI Prep., (1983) pp. 15–19.

Stryer, "Biochemistry", W.H. Freman * Co., (1975), pp. 636.

* cited by examiner

FIG. 1A

```
1   atccactcaggtctacaggtctcttagaactagaacttagaacttatcttgaaaatgtac 122 aagaagtgttcaccacatagttgcaaaggtcttcaactgccacagccaacagagaaaat 242 GCTTTTGAGGAAAATCATAAAAGACAGGAAGACATCATAGACATTTCTGGATCATCT
1    A  F  E  E  N  H  K  K  T  G  R  H  H  K  T  F  L  D  H  L 362 ATAGCATCTTGGTTGCCAGCATACCGGCTTAAAGAATGGTTGCTCAGTGATATTGTTTC
20   I  A  S  W  L  P  A  Y  R  L  K  E  W  L  L  S  D  I  V  S 482 ATTCCCCCAGTCTATGGGTTGTATGCATCCTTTTCCCAGCCATAATCTACCTTTTCTT
60   I  P  P  V  Y  G  L  Y  A  S  F  F  P  A  I  I  Y  L  F  F 602 GCAGTTTCAGGAGCAGTTTCAAAAGCAGTCCCAGATCGCAATGCAACTACTTTGGGATT
100  A  V  S  G  A  V  S  K  A  V  P  D  R  N  A  T  T  L  G  L
140
```

FIG. 1B

```
cactgttgcagaagctcctcacagagtatgtgtcaggcattttaacctgctaaaggcaag caaaATGATTGAACCCTTTGGGAATCAGTATATTGTGGCCAGTGTATTCTACAAAT
     M  I  E  P  F  G  N  Q  Y  I  V  A  R  P  V  Y  S  T  N CAAAGTGTGTGTAGCTGTTCCCCACAAAGGCCAAGAGAATTGTCCTCTCTTGTTCCCC
 K  V  C  C  S  C  S  P  Q  K  A  K  R  I  V  L  S  L  F  P TGGTATCAGCACAGGGATTGTGGCCGTACTACAAGGTTTAGCATTTGCTCTCTGGTCGAC
 G  I  S  T  G  I  V  A  V  L  Q  G  L  A  F  A  L  L  V  D CGGCACTTCCAGAGACACATATCCGTGGGTTTCCGTTTCCGATTCTGAGTATGATGGGACTA
 G  T  S  R  H  I  S  V  G  P  F  F  P  I  L  S  M  M  V  G  L GCCTAACAACTCGAATAATTCTTCACTACTGGATGACGAGAGGGTGAGGGTGGCGGGGCG
 P  N  N  S  N  N  S  S  L  L  D  D  E  R  V  R  V  A  A  A
```

FIG. 1C

```
 722  GCATCAGTCACAGTGCTTTCTGGAATCATCCAGTTGGCTTTTGGATTCTCGGATTGG
 180   A  S  V  T  V  L  S  G  I  I  Q  L  A  F  G  I  L  R  I  G

842  CATGTTTTGGTTTCCCAACTCAAATTCATTTTTCAGTTGACAGTCCCGTCACACACTGA
 220   H  V  L  V  S  Q  L  K  F  I  F  Q  L  T  V  P  S  H  T  D

962  GCAGACCTGGTGACAGCTCTGATTGTCCTTTTGGTTGTATCCATTGTTAAGAAATAAA
 260   A  D  L  V  T  A  L  I  V  L  L  V  V  S  I  V  K  E  I  N

1082  GCAGCAGGTGTATCCTACGGCTGTGACTTTAAAAACAGGTTTAAAGTGGCTGTGGTTGG
 300   A  A  G  V  S  Y  G  C  D  F  K  N  R  F  K  V  A  V  V  G

1202  GTAGGAGAATTGCTTCGGCATCGCAATGGTTGCATTTGCAGTGGCCTTTTCAGTTGCCAG
 340   V  G  D  C  F  G  I  A  M  V  A  F  A  V  A  F  S  V  A  S

1322  CTGGGTAACATAGTCTGTGGAGTATTCAGAGGATTGCTGGGAGTACTGCCCTCTCCAG
 380   L  G  N  I  V  C  G  V  F  F  R  G  F  A  G  S  T  A  L  S  R
```

FIG. 1D

```
ATTTGTAGTGATATACCTGTCTGAGTCCCTCATCAGTGGCTTCACTACTGCTGCTGTT
 F  V  V  I  Y  L  S  E  S  L  I  S  G  F  T  T  A  A  V

TCCAGTTTCAATTTCAAAGTACTATACTCTGTATTCTCACAAATAGAGAAGACTAATATT
 P  V  S  I  F  K  V  L  Y  S  V  F  S  Q  I  E  K  T  N  I

TCAGCGCTTCAAAGACAAACTTCCAGTGCCCATTCCAATCGAATTCATTATGACCGTGATT
 Q  R  F  K  D  K  L  P  V  P  I  P  I  E  F  I  M  T  V  I

GGACATGAATCCTGGATTTCAGCCCCTATTACACCTGACGTGGAGACTTTCCAAACACC
 D  M  N  P  G  F  Q  P  P  I  T  P  D  V  E  T  F  Q  N  T

CGTCTATTCCCTCAAATATACGATTATCCACTTGATGGCAATCAGGAGTTAATAGCCTTGGGA
 V  Y  S  L  K  Y  D  Y  P  L  D  G  N  Q  E  L  I  A  L  G

ATCAGCAGTTCAGGAGAGCACAGGAGGCAAAACACAGATTGCTGGGCTTATTGGTGCCATC
 S  A  V  Q  E  S  T  G  G  K  T  Q  I  A  G  L  I  G  A  I
```

FIG. 1E

```
1442  ATCGTGCTGATTGTCGTTCTAGCCATTGGATTTCTCCTGGCGCCTCTACAAAGTCCGT
       ----------+---------+---------+---------+---------+---------+
 420   I  V  L  I  V  V  L  A  I  G  F  L  L  A  P  L  Q  K  S  V

1562  AGATTGTGGCGAAAGGACAAATATGATTGTTAATTGGATCATGACCTTCATCTTCAC
       ----------+---------+---------+---------+---------+---------+
 460   R  L  W  R  K  D  K  Y  D  C  L  I  W  I  M  T  F  I  F  T

1682  GTGTTCAGGACCCAATTTCCAAATGCAGCTGGCTAATATTGGAAGAACCAACAT
       ----------+---------+---------+---------+---------+---------+
 500   V  F  R  T  Q  F  P  K  C  S  T  L  A  N  I  G  R  T  N  I

1802  TGTCCATCTCCTATCTACTTTGCAAACATTGGTTTCTTTAGGCGGAAACTTATCGATGC
       ----------+---------+---------+---------+---------+---------+
 540   C  P  S  P  I  Y  F  A  N  I  G  F  F  R  R  K  L  I  D  A

1922  AAACTGCAGAAGCAAGGCTTGCTACAAGTGACACCAAAAGGATTTATATGTACTGTTGA
       ----------+---------+---------+---------+---------+---------+
 580   K  L  Q  K  Q  G  L  L  Q  V  T  P  K  G  F  I  C  T  V  D

2042  ATCAATACCACAGACCTGCCTTTCCACATTGACTGGAATGATGATCTTCCTCTCAACAT
       ----------+---------+---------+---------+---------+---------+
 620   I  N  T  T  D  L  P  F  H  I  D  W  N  D  D  L  P  L  N  I
```

FIG. 1F

```
CCTGGCAGCTTTAGCATTGGGAAACTTAAAGGGAATGCTGATGCAGTTTGCTGAAATAGGC
 L  A  A  L  A  L  G  N  L  K  G  M  L  M  Q  F  A  E  I  G

CATTGTCCTGGGACTCGGGGTTAGGCCTGGCAGCTAGTGTGGCATTTCAACTGCTACCATC
 I  V  L  G  L  G  L  A  A  S  V  A  F  Q  L  L  T  I

CTATAAGAATAAAAAAGATTATTATGATATGTATGAGCCAGAAGGAGTGAAAATTTCAGA
 Y  K  N  K  K  D  Y  Y  D  M  Y  E  P  E  G  V  K  I  F  R

TGTTGGCTTTAGTCCACTTCGAATTCTACGCAAGCGCAACAAAGCTTTGAGGAAAATCCGA
 V  G  F  S  P  L  R  I  L  (R  K  R  N  K) A  L  (R  K  K  I  (R

CACCATAAAAGATTCTGACGAAGAGCTGGACAACAATCAGATAGAAGTACTGGACCAGCCA
 T  I  K  D  S  D  E  E  L  D  N  N  Q  I  E  V  L  D  Q  P

TGAGGTCCCCAAAATCAGCCTCCACAGCCTCATTCTCGACTTTTCAGCAGTGTCCTTTCTT
 E  V  P  K  I  S  L  H  S  L  I  L  D  (F  S  A  V  S  F  L
```

FIG. 1G

```
2162  GATGTTCTTCAGTGAGGGCCCTAAATCGATTTGCAAGAATTTATCAGGATCAAGGT
 660    D   V   S   S   V   R   G   L   K   S   I   L   Q   E   F   I   R   I   K   V

2282  TTTGATGGTGAAGTGAAAAGCTCAATATTTTCTTAACAATCCATGATGCTGTTTGCA
 700    F   D   G   E   V   K   S   S   I   F   F   L   T   I   H   D   A   V   L   H

2402  AAAATTGATTTTACCATAAATACAAATGGAGGATTACGTAATCGGGTATATGAGGTGCC
 740    K   I   D   F   T   I   N   T   N   G   G   L   R   N   R   V   Y   E   V   P 2522  aaaacaactttataccagaaagttattgataagttcatacacattgtacgaaagagtatt 2642  atctagtatgaaattatataagtattctaaatttatatcttgtagcttatcaaagg 2762  ccttcatgcataggtttagcagtatagtggccgccactgtttgaatctcataattata 2882  a    2882
```

FIG. 1H

```
AGATGTGTATATCGTTGGAACTGATGATGACTTCATTGAGAAGCTTAACCGGTATGAATTT
 D  V  Y  I  V  G  T  D  D  D  F  I  E  K  L  N  R  Y  E  F

TATTTGATGAAGAAAGATTACAGTACTTCAAAGTTTAATCCCAGTCAGGAAAAGATGGA
 I  L  M  K  K  D  Y  S  T  S  K  F  N  P  S  Q  E  K  D  G

AGTTGAAACAAAATTCTAAtcaacatataattcagaaggatcttcatctgactatgacata
 V  E  T  K  F ttgacagaatatgttttcaaactttggaacaagatggttctagcatggcatatttttcacat tgaaaattatttttgttcatacatattttttgtagcactgacacagatttccatcctagtcacta caggtcatattaatatattttccattaaaaatcagttgtacagttgtgaaaaaagaaa
```

FIG. 2

|   |   |   |   |   |
|---|---|---|---|---|
| R | I | L | R | N K |
| K | A | L | R | K |
|   | R | I | R | K L Q K |
| R | W | G | K | R N K |
| G | G | P | K | K R K |

DRA$_{566-573}$
DRA$_{573-580}$
DRA$_{576-583}$
ets1, 2
SV40 T

FIG. 3

```
DRA620-640   I N T T D L P F - H I D W N D D L P L N E
VP16         L D G E D V A M A H A D A L D D F D L D M L
SP1(A)       L Q N Q Q L T G L P G V M P N I Q Y V I
SP1(B)       I R T P T V G P N G Q V S W Q T L Q L Q N L
```

METHODS FOR EVALUATING COLON TISSUE FOR EXPRESSION OF THE DRA (DOWN REGULATED IN ADENOMA) GENE

This is a divisional of U.S. application Ser. No. 08/711,928, filed Sep. 11, 1996, issuing Nov. 3, 1998 as U.S. Pat. No. 5,831,015, which is a divisional of application Ser. No. 08/424,567, filed Apr. 17, 1995, issuing Oct. 29, 1996 as U.S. Pat. No. 5,569,755, which is a continuation of application Ser. No. 08/026,045, filed Mar. 5, 1993, now abandoned.

BACKGROUND OF THE INVENTION

Colorectal cancer is a significant cancer burden to the general population of many developed countries. In the United States alone, there are over 130,000 new cases of colorectal cancer per year, and over 65,000 deaths per year resulting from colorectal cancer. Colorectal cancer it is second only to lung cancer in cancer morbidity in the United States.

The progression of colorectal cancer, or colorectal tumorigenesis, is a multi-step process involving the loss of function of so-called tumor suppressor genes, as well as the activation of oncogenes. Fearon et al., *Cell* 61: 759–67 (1990); Paraskeva et al., *Anticancer Research* 10: 1189–200 (1990). It is also marked by several phenotypically distinct stages during progression. These include normal, hyperplastic, benign, carcinoma and metastatic stages. These distinct stages make colorectal cancer an exceptionally useful paradigm for the studying the molecular genetic basis of cancer in general.

Among the classical oncogenes implicated in cancer, the ras and myc genes have been found to be activated and/or show elevated expression in colorectal tumors. About half of large adenomas and at least half of carcinomas contain activated K-ras genes. Forrester et al., *Nature* 327: 298–303 (1987); Bos et al., *Nature* 327: 293–97 (1987); Burmer et al., *Proc. Nat'l Acad. Sci. USA* 86: 2403–07 (1989). C-myc over expression and occasional gene amplification have also been demonstrated in colorectal tumors. Erisman et al., *Mol. Cell. Biol.* 5: 1969–76 (1985); Imaseki et al., *Cancer* 64: 704–09; Finley et al., *Oncogene* 4: 963–71 (1989). Furthermore, deregulated c-myc expression can be suppressed by microcell-mediated transfer of chromosome 5, which is the locus for the putative tumor-suppressor genes, APC (for adenomatous polyposis coli) and MCC (for mutated in colorectal carcinoma) discussed below. Rodriguez-Alfageme et al., *Proc. Nat'l Acad. Sci. USA* 89: 1482–86 (1992). Although the importance of oncogenes in cancer development can not be ignored, it is the presently the tumor suppressor genes which have drawn the most interest for study of cancer development.

Several tumor suppressor genes have been implicated in colorectal tumor progression. One of the more noteworthy tumor suppressor genes is p53. This gene has a locus at chromosome band 17p13 and is lost in a large majority of colon carcinomas (though not as much in adenomas). Often the lesion, which refers to genetic mutations, consists of a deletion of one allele and a point mutation at one of several hotspots in the remaining allele. Baker et al., *Science* 244: 217–21 (1989), Nigro et al., *Nature* 342: 705–07 (1989). Importantly, it has been shown that transfection of a wild-type p53 gene into colon cancer cell lines in vitro results in a suppression of cell growth, thereby demonstrating that the p53 gene product, a tumor suppressor, has a direct effect on one major cancer characteristic. Baker et al., *Science* 249: 912–15 (1990).

Genes APC and MCC identified above have been mapped to a locus at chromosome band 5q21. Groden et al., *Cell* 66: 589–600 (1991); Kinzler et al., *Science* 253: 661–64 (1991); Kinzler et al., *Science* 251: 1366–70 (1991). This is the site which is linked to the inherited disorder adenomatous polyposis coli, which is a disorder marked by multiple polyposis and a very high incidence of colon carcinoma at an early age. Both genes contain mutations and/or deletions in colon carcinoma, however, MCC mutations are not common among tumors, whereas the APC lesions are more common and found in the germ line genomic DNA of APC patients. Kinzler et al., *Science* 251: 1366–70 (1991); Nishisho et al., *Science* 253: 665–69. It is notable that transfer of chromosome 5 to colon cancer cells lacking a normal APC gene suppresses tumorigenicity. Goyette et al., *Mol. Cell. Biol.* 12: 1387–95 (1992). This reinforces the concept that APC and/or MCC are tumor suppressor genes. Another gene, the DCC gene (for deleted in colorectal carcinoma), is located at chromosome band 18q21 and also is lost in a large majority of colon carcinomas and about fifty percent of late adenomas. A portion of the DCC gene bears a homology to the neural cell adhesion molecule (N-CAM). Fearon et al., *Science* 247: 49–56 (1990). This suggests that the DCC gene product may play a role in cell-to-cell contacts. A specific role in colorectal tumor progression, however, has not been ascertained.

The identification of such genes, the absence or impairment of which is linked to cancer, yields insights into the initiation and progression of cancer and other abnormalities. Additionally, the existence of such genes raises the possibility that other tumor suppressor genes may exist.

SUMMARY OF THE INVENTION

It is therefore an object of the present invention to identify a gene that is down-regulated in colon adenomas and adenocarcinomas.

Another object of this invention is to provide a gene that is down-regulated early in tumorigenesis.

It is another object of this invention to provide a cDNA sequence that corresponds to the aforementioned down-regulated gene.

Still another object of this invention to provide a nucleotide probe that hybridizes to the aforementioned down-regulated gene.

Still another object is to provide for a down-regulated gene herein referred to as "DRA" (for down regulated in adenoma).

It is yet another object of this invention is to provide a method for identifying and isolating candidate tumor suppressor genes.

It is still another object of this invention to provide an assay and method to diagnose and/or identify colon tissue abnormalities by measuring the presence or absence of the mRNA or protein product of a down-regulated gene.

In accomplishing the foregoing objects, there has been provided, in accordance with one aspect of the present invention, a cDNA encoding a polypeptide having a molecular weight of about 84,500 daltons. The mRNA encoding this polypeptide has been found to be down-regulated in adenocarcinomas and adenomas of the colon.

There is also provided a method for evaluating colon tissue comprising the steps of:

obtaining a colon tissue test sample;

evaluating the amount of DRA mRNA expression in, said colon tissue sample by hybridizing the mRNA of said tissue sample with a nucleotide probe derived from the DRA nucleotide sequence;

comparing said amount of DRA mRNA expression in said colon tissue sample to a control to determine relative DRA mRNA expression.

Other objects, features and advantages of the present invention will become apparent from the following detailed description, sequence data and tables.

BRIEF DESCRIPTION OF THE FIGURES

FIGS. 1A–1L depicts the DRA nucleotide sequence and predicted amino acid sequence of the DRA protein (SEQ ID NOS 1 and 2). FIG. 1K illustrates how FIGS. 1A–1J combine to depict these sequences.

FIG. 2 depicts alignment of nuclear targeting motifs. The sequences shown in this Figure correspond to residues 566–573 of SEQ ID NO: 2, residues 573–580 of SEQ ID NO: 2, residues 576–583 of SEQ ID NO: 2, SEQ ID NO: 3 and SEQ ID NO: 4.

FIG. 3 depicts alignment of acidic transcriptional activation domains. The sequences shown in this Figure correspond to residues 620–640 of SEQ ID NO: 2, SEQ ID NO: 5, SEQ ID NO: 6 and SEQ ID NO: 7.

DETAILED DESCRIPTION OF PREFERRED EMBODIMENTS

A new down-regulated gene called "DRA" (for down regulated in adenoma) has been discovered which maps to chromosome 7. Thus, a DRA cDNA clone has been identified and isolated by "subtractive hybridization," a technique that does not require extensive information, such as incidence of heterozygosity loss, to identify candidate tumor suppressor genes. Schweinfest et al., *Intn'l J. Oncology* 1: 499–506 (1992); Lee et al., *Proc. Nat'l Acad. Sci. USA* 88: 2825–29 (1991). Similarly, subtractive hybridization does not require informative loci for restriction fragment length polymorphism analysis. Rather, it only requires that mRNA expression differ in two tissue sources.

The DRA nucleotide sequence (SEQ ID NO: 1) encodes a polypeptide (SEQ ID NO: 2) having a predicted molecular weight of about 84,500 daltons, which is believed to be a tumor suppressor. The mapping of the DRA gene to chromosome 7 is of interest because abnormalities in this chromosome have been associated with colorectal carcinomas. Paraskeva et al., *Anticancer Research* 10: 1189–200 (1990); Rau et al., *Anticancer Research* 11: 1477–84 (1991). But chromosome 7 to date has not been identified as a locus for a colon cancer tumor suppressor gene.

The DRA gene and gene product have several other interesting characteristics. For instance, the DRA gene encodes a hydrophobic protein ("the DRA polypeptide") with charged clusters located in the carboxyl terminus. Additionally, the normal expression of the DRA gene expression product appears to be limited strictly to the mucosa of normal colon, which is typically the origin of colonic neoplasms. The pattern of down regulation shows that DRA expression is lost early in tumorigenesis.

The present disclosure of the DRA cDNA sequence permits large-scale expression of the DRA polypeptide by recombinant DNA methods. The DRA polypeptide thereby can be obtained in an isolated form by known recombinant methods. The term "isolated" in the context of proteins denotes a degree of purification such that the DRA polypeptide is free at least of other human proteins, as would occur when the DRA polypeptide is produced in known protein expression hosts such as *E. coli*, yeast and CHO cells. The isolated DRA polypeptide preferably would be in homogeneous form, that is, in a form amenable to protein sequencing on a gas-phase sequenator, which are available from manufactures such as Applied Biosystems, Inc. Techniques for obtaining such homogeneity after recombinant production include SDS-PAGE, isoelectric focusing, chromatographic electrophoresis, ion exchange chromatography, gel exclusion chromatography, affinity chromatography, immunoprecipitation, and combinations thereof.

The isolated DRA polypeptide can be used for further study of the process of tumorigenesis and the suppression or prevention thereof. Additionally, it is reasonable to predict that the DRA gene and/or polypeptide may have therapeutic attributes as well.

The pattern of DRA down-regulated expression also can serve as a useful diagnostic indicator of the present and anticipated future state of a sample of colon tissue. For instance, if a colon tissue sample that normally would be expected to express DRA does not express DRA or expresses DRA at lower than normal levels, such information would be an indicator that the tissue has entered tumorigenesis.

The DRA cDNA sequence (SEQ ID NO: 1) has an open reading frame encoding 764 amino acids (SEQ ID NO: 2), including the initiation methionine. The DRA polypeptide contains several amino acid sequences of interest.

The predicted DRA polypeptide based on the cDNA sequence has three potential nuclear targeting motifs as well as a potential acidic transcriptional activation domain and a homeobox domain. The predicted DRA protein has a mass of about 84,500 daltons. It contains clusters of charged amino acid residues at its $NH_2$ and COOH terminal regions, primarily at the COOH terminus starting from amino acid $arg^{460}$. The central region (amino acids $Val^{176}$-$Gly^{459}$, residues 176–459 of SEQ ID NO: 2) is largely hydrophobic, although it is occasionally interrupted by islands of charged clusters.

Casein kinase II and phosphokinase C phosphorylation sites also are clustered predominantly within the COOH terminal region ($Arg^{460}$-$Phe^{764}$, residues 460–764 of SEQ ID NO: 2), while asparagine-linked glycosylation sites are almost all (4 of 5) with the $NH_2$ terminal region ($Met^1$-$Arg^{175}$, residues 1–175 of SEQ ID NO: 2).

The presence of amino acid sequences with known purposes in the DRA polypeptide is highly suggestive of a functional protein that plays a role in the prevention of tumorigenesis. This role correlates well with the observed early down-regulation of DRA expression in tissue abnormalities such as colon adenomas and adenocarcinomas.

Procedures outlined below illustrate how DRA was identified, obtained and characterized; however, it must be understood that this exemplification does not limit the invention as claimed.

Isolation of DRA cDNA

Isolation of a DRA cDNA was undertaken in the following manner. The vector λZAPII was used for construction of cDNA libraries for normal colon and adenocarcinoma tissues using the method of Schweinfest et al., *Genet. Anal. Tech. Appl.* 7: 64–70 (1990).

Generation of subtracted single-stranded phagemid cDNA populations enriched for normal and adenocarcinoma sequences are also described therein. Subtracted single-stranded cDNA inserts were amplified by the polymerase chain reaction ("IPCR") using the KS and SK sequencing primers supplied by the manufacturer (Stratagene). Amplification proceeded for 30 cycles (1 minute at 94° C., 2 min. at 45° C., 3 minutes at 71° C.). Amplified cDNA was labeled with $^{32}$P by the method of Feinberg et al., *Anal. Biochem.* 132: 6–13 (1983), except that the KS primer was used as a specific primer rather than using random primers. Differential plaque hybridization was performed on duplicate lifts from a total of 5×10$^5$ plaques (amplified once) of normal colon λZAPII library. Hybridization with the enriched normal and adenocarcinoma probes was performed in the presence of 10 μg/ml denatured, unlabeled pBluescript DNA in a solution containing 50% deionized formamide, 4×SSPE (1×=180 mM NaCl, 10 mM sodium phosphate, pH 7.4), 5×Denhardt's solution (1×=0.02% bovine serum albumin, 0.02% polyvinylpyrrolidone, 0.02% Ficoll), 100 μg/ml denatured salmon sperm DNA, and 0.5% SDS. Plaques which appeared to hybridize differentially with the two probes were purified through two subsequent rounds of plaque hybridization at lower densities, and rescued as pBluescript phagemid clones according to the manufacturer's protocol (Stratagene). Seven clones showed a strong differential hybridization in favor of the normal-enriched probe. After a total of three rounds of differential hybridization, four clones were obtained. All were confirmed as differential by using them as probes to Northern blots of normal and tumor tissue. One such clone, 611, was used to reprobe the normal library in order to find full-length cDNAs. For clone 611, additional clones, ultimately containing the full coding sequence, were isolated by conventional plaque hybridization.

Expression of DRA in Adenocarcinomas

In order to assess whether loss of expression is a general phenomenon of colon adenocarcinomas or merely limited to the particular tumor sample, a battery of matched tumor and normal tissues that were from the same patient were analyzed by Northern blot hybridization for DRA mRNA expression. Messenger RNA for analysis was isolated by first rinsing cultured cells twice in cold phosphate buffered saline. The cells then were lysed in guanidinium isothiocyanate ("GTC") and purified by centrifugation through a CsCl cushion according to the method of Chirgwin et al., *Biochemistry* 18: 5294–99 (1979). Tissue samples were ground to a powder under liquid nitrogen, then lysed in GTC and centrifuged as set forth above. Total RNA (typically 5 μg per sample) was fractionated on 1.2% agarose gels containing 0.66 M formaldehyde (2.2M in the sample) by the method of Lehrach et al., *Biochemistry* 16: 4703–51 (1977). Gels were transferred either to nitrocellulose (in 20×SSPE) or to GeneScreen (in 0.1 M sodium phosphate pH 6.5).

Matched adenocarcinoma and normal tissue mRNA samples were analyzed by hybridization with a 470 bp probe (corresponding to nucleotides 11–481 of DRA). In 8 of the 9 matched samples, the tumor tissues were completely lacking in expression of the single 3.2 kb DRA mRNA. Although all normal colon samples tested express DRA mRNA, it should be noted that the absolute level of DRA expression can vary from sample to sample. By hybridizing the DRA cDNA back to the normal colon cDNA library, it is estimated that the amount of DRA mRNA ranges from 0.01% to 0.1% of the mRNA population. With one exception, all tumor samples show a marked reduction in the amount of DRA mRNA expressed. The tumor that retained a high level of DRA expression was not remarkable for any differences with the other adenocarcinoma samples tested, which included both right and left colon and well-differentiated to poorly-differentiated specimens. It is possible, however, that the DRA-expressing tumor included a significant portion of normal tissue, which would account for the continued presence of DRA mRNA in the total RNA isolated from this particular tumor sample.

DRA expression was found to occur in the mucosal layer of normal colon. In one set of matched samples, the normal tissue sample consisted of only colon mucosal layer that had been dissected away from the underlying tissues. Thus, normal mucosa is shown to express DRA mRNA, whereas tumor tissue does not. At this time, however, it can not be ruled out that layers under the mucosa may also express DRA. The expression of DRA in the colon mucosal layer is noteworthy because the mucosal layer typically is the origin of colonic neoplasms.

Expression of DRA in Adenomas

The observed down-regulation of DRA in adenocarcinomas suggested that DRA also might be down-regulated in other tissue abnormalities such a adenomas. Benign adenomas, often in the form of polyps, were analyzed for DRA mRNA expression by Northern blot analysis. Colon adenoma cell lines VACO235 and VACO330 (Dr. James K. V. Willson, Case Western Reserve University) also were used for this analysis.

Five micrograms of total RNA from adenoma tissue and adenoma cell lines was fractionated on a 1.2% agarose-formaldehyde gel, then transferred to a nitrocellulose filter.

The data from the adenoma tissue and cell lines show that DRA is down-regulated in adenomas. For instance, adenoma tissue samples showed a significant decline or absence of the 3.2 kb DRA mRNA relative to normal tissue. Some adenoma tissues showed a small amount of DRA expression. Again, it is not clear whether the small amounts of observed expression derives from adenoma cells or residual normal mucosa. The villous adenoma-derived cell line, VACO235, still expresses low but detectable amounts of DRA mRNA. Because it is a cell line, the expression thus detected cannot be due to contaminating normal mucosa. Another adenoma-derived cell line, VACO330, does not express detectable amounts of DRA mRNA compared to VACO235 or normal tissue. Doubling the amount of RNA in the VACO330 lane, however, resulted in some trace amount of DRA expression in the VACO330 cells.

Expression of DRA in Other Tissues

Other tissues and tissue cell lines were examined for expression of DRA. Five micrograms of total RNA was fractionated on a 1.2% agarose-formaldehyde gel, and then transferred to a GeneScreen filter. The tested tissues were as follows: normal colon tissue, lung, heart, placenta, spleen, brain, liver, pancreas, bone marrow, peripheral blood leukocytes, testis and ovary. The mRNAs from these tissues were hybridized to central 820 bp fragment of the DRA cDNA (corresponding to nucleotides 1061–1881).

Tissue cell lines (American Type Culture Collection) were fractionated on a 1% agarose-formaldehyde gel, then transferred to a GeneScreen filter. The tested cell lines were as follows: normal colon tissue, CCD841 CoN (normal colon cells, epithelial-like), CCD18Co (normal colon fibroblasts), CCD33 (normal colon), CCD112CoN (normal colon fibroblasts), HISM (human intestinal smooth muscle), RPMI-7666 (lymphoblasts), HS67 (thymus), FHS738.Bl (bladder), WI-38 (lung), Detroit 55 (skin), HBL-100 (breast epithelia) and Hs1.Tes (testis). The mRNA from these cells lines were hybridized with the 470 bp probe.

This analysis of normal tissue showed that only normal colon expresses significant quantities of DRA mRNA. From the testing of cell lines, the results obtained with HISM, CCD18Co, CCD33Co, and CCD112CoN are of particular note. Cell line HISM is derived from intestinal smooth muscle and cell lines CCD18Co, CCD33Co, and CCD112CoN are fibroblast cells derived from normal colon. Interestingly, these cells, which are all derived from regions other than the mucosal epithelia of normal colon, do not express DRA mRNA. CCD841CoN, while epithelial-like in morphology, is lacking any definitive epithelial characteristics (e.g., it does not stain for keratin), so it cannot be concluded to have derived from the mucosal epithelia. Therefore, it appears that expression of DRA mRNA is restricted to normal colon, and probably to the mucosal layer in particular.

The analysis with DRA indicates a very restrictive pattern of normal expression. In fact, only tissue derived from the mucosa of the colon appears to express significant levels of the DRA mRNA. The possibility does exist, however, that very low levels of mRNA may be detected by a more sensitive assay such as RNase protection or by reverse transcription-PCR. The amount of DRA mRNA expressed in different normal colon samples was found to vary widely. While the DRA mRNA was readily detected in most normal samples, some normal tissues had much lower levels of DRA mRNA than others (although still higher than in tumor). This observation is consistent with the observation of Augenlicht et al., who found that the flat "normal" mucosa of patients at risk for hereditary non-polyposis colorectal cancer or adenomatous polyposis coli exhibits molecular expression changes similar to tumor tissue. *Proc. Nat'l Acad. Sci. USA* 88: 3286–89 (1991).

The fact that DRA expression is down-regulated in adenomas and adenocarcinomas may not be due to mutational inactivation at all. Rather, an epigenetic mechanism may apply. While general hypomethylation of the genomic DNA is observed early in colorectal tumorigenesis, DNA methyl transferase transcription has been shown to be increased 15 times in normal-appearing mucosa around benign tumors. Goelz et al., *Science* 228: 187–90 (1985), Feinberg et al., *Cancer Res.* 48: 1159–61 (1988), El-Deiry et al., *Proc. Nat'l Acad. Sci USA* 88: 3470–74. Much higher levels of expression are observed in premalignant polyps (60-fold increase), and even higher levels (200-fold) are reported in adenocarcinomas. This indicates a mechanism whereby down-regulation of the DRA gene may be achieved through specific methylation of CpG sites, presumably in the 5' regulatory regions of the gene.

Sequence of DRA

Full-length clone(s) were sequenced by the dideoxy chain termination method. Sequence analyses (nucleotide and protein) were performed on the University of Wisconsin Genetics Computer Group package at the Advanced Scientific Computer Laboratory, Frederick, MD. See Devereux et al., *Nucleic Acids Res.* 12: 387–95 (1984). The DRA nucleotide sequence is depicted in FIGS. 1A–1J (SEQ ID NO: 1). Non-coding 5' and 3' nucleotides are shown in lower case, coding nucleotides in upper case. The cDNA is 2882 nucleotides in length and contains an open reading frame of 764 amino acids (SEQ ID NO: 2), including the initiation methionine. is 15The sequence of FIGS. 1A–1J now has a GenBank accession number of L02785.

It must be understood that sequences substantially the same as the nucleotide and amino acid sequences in FIGS. 1A–1J (SEQ ID NO: 1 and 2) may be constructed which would have the function or characteristics of the respective sequences in FIGS. 1A–1J (SEQ ID NOS 1 and 2). This can be the result of known phenomena such as degeneracy in the genetic code, conservative amino acid substitutions, and the existence of non-essential amino acids. Therefore, alterations that do not deleteriously affect the functions or characteristics of the nucleotide sequence (for example, in the context of hybridization) or the polypeptide (for example, with respect to antigenic determinants or functional domains) are within the scope of the present invention.

The DRA polypeptide product, as deduced from the DRA nucleotide sequence, is also presented in FIGS. 1A–1J (SEQ ID NOS 1 and 2).

This polypeptide contains several amino acid motifs of interest. Three potential nuclear targeting motifs at amino acids 569–573, 576–580, 579–583 are shown enclosed with brackets ([ ]) in FIGS. 1A–1J (SEQ ID NOS 1 and 2). Each of these amino acid motifs show conformation to the consensus sequence (see FIG. 2, residues 566–573 of SEQ ID NO: 2, residues 573–580 of SEQ ID NO: 2, residues 576–583 of SEQ ID NO: 2, SEQ ID NO: 3 and SEQ ID NO: 4). One such motif in particular ($Arg^{569}$-$Lys^{573}$, residues 569–573 of SEQ ID NO: 2), closely conforms to the consensus sequence (R,K,T,A)KK(R,Q,N,T,S,G)K (SEQ ID NO: 6). Gomez-Marquez et al., *FEBS Lett.* 2226: 217–19 (1988). A conservative arginine for lysine substitution is the only change found. The other two potential nuclear targeting sites have a less conservative single amino acid substitution (see FIG. 2).

One potential homeobox domain at amino acids $Phe^{653}$-$Arg^{676}$ (residues 653–676 of SEQ ID NO: 2) is shown enclosed by parentheses (FIGS. 1A–1J). This domain includes a helix-turn-helix domain and mismatches the consensus by only a single conservative substitution ($Leu^{667}$ for Trp at residue 667 of SEQ ID NO: 2).

Other sequences of interest are present as well. One potential acidic transcriptional activation domain at amino acids $Ile^{620}$-$Glu^{640}$ (residues 620–640 of SEQ ID NO: 2) is shown underlined in FIG. 3. Additionally, there are two in-frame stops prior to the initiation methionine and nine stops following the TAA codon. A polyadenylation signal, ATTAAA, is found 24 nucleotides upstream from the poly (A) tail.

The sequence around the initiation methionine is TCAAA ATGA (bases 180–188 of SEQ ID NO: 1), which does not conform to the Kozak consensus sequence of CC(A or G)CC ATGG for initiation. Kozak, *J. Cell Biol.* 115: 887–903 (1991). Because two in-frame stops precede this methionine and the next methionine is encoded within the sequence CTGAGTATGA (bases 581–590 of SEQ ID NO: 1), there is no more likely candidate for initiation, however. Importantly, it does contain the crucial A residue at position −3. But the G at position +4 of the consensus, which is also an important residue for translation initiation, does not exist in the DRA sequence; rather, it is replaced by A. Nonetheless, of 699 sequences compiled by Kozak, 114 functional initiator codons contain A residues at positions −3 and +4. In fact, the human α-amylase and α-lactalbumin mRNAs exactly match the sequence of the DRA mRNA at positions −4 to +4. Kozak, *Nucleic Acids Res.* 15: 8125–48 (1987). Finally, it cannot be ruled out that a GTG codon at amino acid $Val^{11}$ could be utilized as a non-ATG initiation site. Kozak, *Mol. Cell. Biol.* 9: 5073–80 (1989).

A search of the GenBank and EMBL nucleotide data bases failed to reveal any other sequences to which DRA has any significant homology. Additionally, no significant homologies were found when the open reading frame was used to search the protein data bases. The predicted DRA protein has a mass of about 84,500 daltons. It contains clusters of charged amino acid residues at its $NH_2$ and COOH terminal regions, primarily at the COOH terminus starting from amino acid arg. The central region (amino acids $Val^{176}$-$Gly^{459}$ residues 176–459 of SEQ ID NO: 2) is largely hydrophobic, although it is occasionally interrupted by islands of charged clusters. Casein kinase II and phosphokinase C phosphorylation sites are also clustered predominantly within the COOH terminal region ($Arg^{460}$-$Phe^{764}$, residues 460–764 of SEQ ID NO: 2), while asparagine-linked glycosylation sites are almost all (4 of 5) with the $NH_2$ terminal region ($Met^1$-$Arg^{175}$, residues 1–175 of SEQ ID NO: 2)

The open reading frame of the DRA nucleotide sequence has been verified by in vitro translation and SDS-PAGE of in vitro transcribed DRA mRNA. Furthermore, polyclonal antibodies directed against several short peptides ($\leq 20$ amino acids) from the carboxyl-terminal one-third of the protein react with a truncated version of DRA expressed in *E. coli*. The deduced DRA polypeptide contains several noteworthy motifs suggestive of transcription factors or of proteins which interact with transcription factors. The COOH end of the protein contains numerous charged amino acid residues. Other charge clusters are distributed at discrete locations throughout the molecule. Such charge clusters have been noted in functional domains of transcription factors. Brendel et al., *Proc. Nat'l Acad. Sci. USA* 86: 5698–5702 (1989). The COOH terminal half of the DRA polypeptide contains three potential nuclear targeting motifs discussed above (FIG. 2, residues 566–573 of SEQ ID NO: 2, residues 573–580 of SEQ ID NO: 2, and residues 576–583 of SEQ ID NO: 2). Human ets1 and ets2 (SEQ ID NO: 3) as well as the SV40 T antigen (SEQ ID NO: 4), all of which are known to be localized at the nucleus, are shown for comparison. The DRA polypeptide also has an acidic region (residue 620–640 of SEQ ID NO: 2 FIG. 3), which may serve as a transcriptional activation domain similar to that reported for the HSV-1 VP16 protein (SEQ ID NO: 5). Cress et al., *Science,* 251: 87–90 (1991). Human SP1(A)(SEQ ID NO: 6); and SP1(B) (SEQ ID NO: 7) are also shown for comparison. The distinguishing characteristic of the motif in FIG. 3 is "bulky" hydrophobic amino acids (shown in boxes) flanked by amino acids with carbonyl-containing side groups (shown underlined).

It is of interest, however, that no leucine zipper or zinc finger motifs have been observed in the DRA polypeptide. Furthermore, it can be estimated that the DRA mRNA is approximately 0.01 to 0.1% of the mRNA population. This may be rather high for a transcription factor. By comparison, Sp-1 comprises approximately 0.003% of HeLa cell protein and Ap-1 comprises up to 0.005% of HeLa cell protein. Briggs et al., *Science* 234: 47–52 (1986), Lee et al., *Cell* 49: 741–52 (1987). Therefore, the suggestion that the DRA protein is a transcription factor or a protein which interacts with transcription factors requires confirmation.

Chromosomal Location of DRA

Chromosome location of the DRA gene was investigated by hybridizing a central EcoRI fragment of the DRA cDNA to two panels of somatic cell hybrid genomic DNAs (chromosome blots CB-2A-I and CB-2B-I) from BIOS of New Haven, CT. Hybridization was performed for two hours in QuikHyb solution (Stratagene) according to the manufacturer's procedure. The hybridization results to each panel was scored blindly and separately from one another. Both panels indicated that the DRA gene is located on chromosome 7. There was 100% concordance for chromosome 7 and 100% discordance for all other chromosomes.

Chromosome 7 has not been previously associated with tumor progression in colorectal carcinoma through gene loss. However, it has been reported both polysomies and monosomies of chromosome 7 in various cultured colorectal cell lines that represent different stages of tumorigenic progression. Paraskeva et al., *Anticancer Res.* 10: 1189–1200 (1990). Polysomies of chromosome 7, as well as breakpoints at chromosome 7p in colon carcinoma cells, have been reported by other investigators as well. Rau et al., *Anticancer Res.* 11: 1477–84 (1991). Significantly, the only adenoma sample in which significant DRA expression was observed, VACO235, contains a translocation of extra material to chromosome 7q. In contrast, the adenoma cell line, VACO330, which does not express DRA, has a normal diploid karyotype. Willson et al., *Cancer Res.* 47: 2704–13 (1987). No gross rearrangements of DRA genomic DNA in VACO235 or in any of several colon carcinoma cell lines tested were detected. Therefore, the mechanism for the loss of DRA expression is more subtle. Possible mechanisms include a small mutation (transition or deletion). Such molecular lesions may be detected by single-stranded conformation polymorphism, denaturing gradient gel electrophoresis or by direct sequencing of the DNA in non-expressing cell lines.

Uses of DRA

The observed down-regulation of DRA mRNA expression in colonic abnormalities endow the gene, cDNA, mRNA and polypeptide with many uses, both diagnostic and possibly therapeutic.

For example, the absence of DRA mRNA expression in colon adenomas and adenocarcinomas makes DRA a useful diagnostic indicator of colon cancer and other colon abnormalities. This absence (down-regulation) occurs in the beginning of the development of the cancer or abnormality; thus, DRA down-regulation will be useful for early detection and analyses of such cancers or abnormalities.

Nucleotide probes ("DRA probes") may be synthesized according to the DRA sequence listed in FIGS. 1A–1J (SEQ ID NO: 1) via methods known to those skilled in the art. These DRA probes can then be used to screen colon tissue samples for the absence or presence of DRA mRNA. As shown herein, the absence or down-regulation of DRA mRNA in tissue normally expressing DRA mRNA is closely correlated with colorectal tissue abnormalities. Such absence or down-regulation can be determined by comparing the amount or degree of DRA mRNA expression in a suspected colonic mucosal tissue abnormality (for example, a polyp) to the amount or degree of DRA mRNA expression in the surrounding normal colonic mucosal tissue. Thus, the DRA probes can be used to ascertain the status of colon tissue and can be predictors of future tissue changes.

A variety of probe sizes and hybridization conditions are amenable to diagnostic uses. Polynucleotide probes of at least 100 nucleotides in length are preferred, and probes of at least 200 nucleotides in length are more preferred. The sequences contained in FIGS. 1A–1J (SEQ ID NO: 1) permit polynucleotide probes of greater lengths to be obtained (for example, 500 nucleotides), which are even more preferred. These polynucleotide probes would be used under standard hybridization conditions, such as 65° C. in 4×SSPE plus 5×Denhardt's solution. Oligonucleotide probes, usually less than 20 nucleotides in length, also can be used for diagnostic purposes with standard hybridization procedures. In comparison to the longer polynucleotide probes, oligonucleotide probes are typically employed under lower stringency conditions and result in a greater number of false positives. The specificity of oligonucleotide probes can be enhanced, however, by employing sets of nested oligonucleotide probes as primers in rounds of the polymerase chain reaction, which ultimately will selectively amplify the appropriate sequences (DRA).

The cDNA clone disclosed herein also allows production of the DRA polypeptide via known recombinant DNA techniques. Recombinant production methods will allow the DRA polypeptide to be obtained in a purified, isolated form, which will permit further study of the DRA polypeptide structure and function. Additionally, the isolated DRA polypeptide or fragments thereof can be used as antigens for the production of antibodies, including monoclonal antibodies, via known methods. These anti-DRA polypeptide antibodies can be used as a diagnostic tool for detecting the presence or the absence of the DRA polypeptide in a particular tissue sample. The presence or absence of the DRA polypeptide determined through screening with anti-DRA antibodies can also be used to ascertain the status of colon tissue and predict future tissue changes.

The DRA gene, cDNA and polypeptide also may have therapeutic properties. For instance, it may be possible to treat suspect colon abnormalities with the DRA polypeptide to reverse or halt the growth or spread of the abnormality. Conventional recombinant techniques can be used to create a source of purified, isolated DRA polypeptide. Additionally, and perhaps even more significantly, it may be possible to employ emerging gene therapy techniques to insert the DRA gene or cDNA into deficient individuals. Such gene therapy techniques are taught in Culver et al., *Science* 256: 1550–52 (1992). The use of the DRA gene or cDNA in this manner could prevent colon abnormalities from arising in the first place.

While the foregoing has concentrated on the preferred embodiments of the claimed invention, it is to be understood that changes in the construction, combination, selection, and arrangement of the elements of this invention may be resorted to without departing from the scope and spirit of the invention as claimed.

What is claimed is:

1. A method for detecting the presence of a DRA nucleic acid in a biological sample comprising the following steps:
   (a) providing a biological sample;
   (b) providing a nucleic acid probe, wherein the probe consists of from 100 to 2882 consecutive nucleotides of SEQ ID NO: 1, or a sequence fully complementary to a sequence consisting of from 100 to 2882 consecutive nucleotides of SEQ ID NO: 1; and
   (c) contacting the biological sample with the nucleic acid probe and determining whether the probe specifically hybridizes to a nucleic acid in the biological sample, wherein detection of specific hybridization is indicative of the presence of a DRA nucleic acid in the biological sample.

2. The method of claim 1, wherein the nucleic acid probe consists of SEQ ID NO: 1 or a sequence fully complementary to SEQ ID NO: 1.

3. The method of claim 1, wherein the nucleic acid probe consists of nucleotides 185–2479 of SEQ ID NO: 1 or a sequence fully complementary to nucleotides 185–2479 of SEQ ID NO: 1.

4. The method of claim 1, wherein the nucleic acid probe consists of nucleotides 11–481 of SEQ ID NO: 1 or a sequence fully complementary to nucleotides 11–481 of SEQ ID NO: 1.

5. The method of claim 1, wherein the biological sample comprises a colon cell.

6. The method of claim 1, wherein the biological sample comprises a colon polyp cell.

7. A method for determining the level of DRA mRNA expression in a colon tissue sample comprising the following steps:
   (a) providing a first sample comprising a test colon tissue sample and a second sample comprising a normal colon tissue sample;
   (b) providing a nucleic acid probe, wherein the probe consists of a sequence fully complementary to a sequence consisting of from 100 to 2882 consecutive nucleotides of SEQ ID NO: 1;
   (c) contacting the nucleic acid probe with equal amounts of mRNA from the first sample and the second sample;
   (d) determining the amount of probe that specifically hybridizes to mRNA from the first sample and to mRNA from the second sample; and
   (e) comparing the amount of probe specifically hybridizing to mRNA from the first sample to the amount of probe specifically hybridizing to mRNA from the second sample, thereby determining the level of DRA mRNA expression in a colon tissue sample.

8. The method of claim 7, wherein the hybridization of a smaller amount of probe to mRNA from the first sample than to mRNA from the second sample is indicative that expression of DRA mRNA is down-regulated in the first sample.

9. The method of claim 7, wherein the nucleic acid probe consists of a sequence fully complementary to SEQ ID NO: 1.

10. The method of claim 7, wherein the nucleic acid probe consists of a sequence fully complementary to nucleotides 185–2479 of SEQ ID NO: 1.

11. The method of claim 7, wherein the nucleic acid probe consists of a sequence fully complementary to nucleotides 11–481 of SEQ ID NO: 1.

12. A method for diagnosis of colon adenoma or colon adenocarcinoma in a patient comprising the following steps:

(a) providing a sample comprising a colon tissue sample from the patient;
(b) providing a nucleic acid probe, wherein the probe consists of a sequence fully complementary to a sequence consisting of from 100 to 2882 consecutive nucleotides of SEQ ID NO: 1;
(c) contacting the nucleic acid probe with mRNA from the colon tissue sample; and
(d) detecting specific hybridization of the probe to the mRNA from the colon tissue sample, wherein the absence of specific hybridization is diagnostic of colon adenoma or colon adenocarcinoma in the patient.

13. The method of claim 12, wherein the nucleic acid probe consists of a sequence fully complementary to SEQ ID NO: 1.

14. The method of claim 12, wherein the nucleic acid probe consists of a sequence fully complementary to nucleotides 185–2479 of SEQ ID NO: 1.

15. The method of claim 12, wherein the nucleic acid probe consists of a sequence fully complementary to nucleotides 11–481 of SEQ ID NO: 1.

* * * * *

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
      (A) LENGTH: 2882 base pairs
      (B) TYPE: nucleic acid
      (C) STRANDEDNESS: double
      (D) TOPOLOGY: linear (ii) MOLECULE TYPE: cDNA (ix) FEATURE:
      (A) NAME/KEY: CDS
      (B) LOCATION: 185..2479

(xi) SEQUENCE DESCRIPTION: SEQ ID NO:1:

```
ATCCACTCAG GTCTACAGGC TCTTAGAACT AGAACTTAGA ACTTTATCTT GAAAATGTAC        60

CACTGTTGCA AAGCTCCTC ACAGAGTATG TGTCAGGCAT TTTTAACCTG CTAAAGGCAA       120

GAAGAAGTGT TCACCACATA GTTGCAAAGG TCTTCAACTT GCCACAGCCA ACAGAAAAAT      180

CAAA ATG ATT GAA CCC TTT GGG AAT CAG TAT ATT GTG GCC AGG CCA GTG       229
     Met Ile Glu Pro Phe Gly Asn Gln Tyr Ile Val Ala Arg Pro Val
      1               5                  10                  15

TAT TCT ACA AAT GCT TTT GAG GAA AAT CAT AAA AAG ACA GGA AGA CAT        277
Tyr Ser Thr Asn Ala Phe Glu Glu Asn His Lys Lys Thr Gly Arg His
                 20                  25                  30

CAT AAG ACA TTT CTG GAT CAT CTC AAA GTG TGT TGT AGC TGT TCC CCA        325
His Lys Thr Phe Leu Asp His Leu Lys Val Cys Cys Ser Cys Ser Pro
                 35                  40                  45

CAA AAG GCC AAG AGA ATT GTC CTC TCT TTG TTC CCC ATA GCA TCT TGG        373
Gln Lys Ala Lys Arg Ile Val Leu Ser Leu Phe Pro Ile Ala Ser Trp
             50                  55                  60

TTG CCA GCA TAC CGG CTT AAA GAA TGG TTG CTC AGT GAT ATT GTT TCT        421
Leu Pro Ala Tyr Arg Leu Lys Glu Trp Leu Leu Ser Asp Ile Val Ser
         65                  70                  75

GGT ATC AGC ACA GGG ATT GTG GCC GTA CTA CAA GGT TTA GCA TTT GCT        469
Gly Ile Ser Thr Gly Ile Val Ala Val Leu Gln Gly Leu Ala Phe Ala
     80                  85                  90                  95

CTG CTG GTC GAC ATT CCC CCA GTC TAT GGG TTG TAT GCA TCC TTT TTC        517
Leu Leu Val Asp Ile Pro Pro Val Tyr Gly Leu Tyr Ala Ser Phe Phe
                100                 105                 110
```

-continued

```
CCA GCC ATA ATC TAC CTT TTC TTC GGC ACT TCC AGA CAC ATA TCC GTG      565
Pro Ala Ile Ile Tyr Leu Phe Phe Gly Thr Ser Arg His Ile Ser Val
            115                 120                 125

GGT CCG TTT CCG ATT CTG AGT ATG ATG GTG GGA CTA GCA GTT TCA GGA      613
Gly Pro Phe Pro Ile Leu Ser Met Met Val Gly Leu Ala Val Ser Gly
        130                 135                 140

GCA GTT TCA AAA GCA GTC CCA GAT CGC AAT GCA ACT ACT TTG GGA TTG      661
Ala Val Ser Lys Ala Val Pro Asp Arg Asn Ala Thr Thr Leu Gly Leu
    145                 150                 155

CCT AAC AAC TCG AAT AAT TCT TCA CTA CTG GAT GAC GAG AGG GTG AGG      709
Pro Asn Asn Ser Asn Asn Ser Ser Leu Leu Asp Asp Glu Arg Val Arg
160                 165                 170                 175

GTG GCG GCG GCG GCA TCA GTC ACA GTG CTT TCT GGA ATC ATC CAG TTG      757
Val Ala Ala Ala Ala Ser Val Thr Val Leu Ser Gly Ile Ile Gln Leu
                180                 185                 190

GCT TTT GGG ATT CTG CGG ATT GGA TTT GTA GTG ATA TAC CTG TCT GAG      805
Ala Phe Gly Ile Leu Arg Ile Gly Phe Val Val Ile Tyr Leu Ser Glu
            195                 200                 205

TCC CTC ATC AGT GGC TTC ACT ACT GCT GCT GCT GTT CAT GTT TTG GTT      853
Ser Leu Ile Ser Gly Phe Thr Thr Ala Ala Ala Val His Val Leu Val
        210                 215                 220

TCC CAA CTC AAA TTC ATT TTT CAG TTG ACA GTC CCG TCA CAC ACT GAT      901
Ser Gln Leu Lys Phe Ile Phe Gln Leu Thr Val Pro Ser His Thr Asp
    225                 230                 235

CCA GTT TCA ATT TTC AAA GTA CTA TAC TCT GTA TTC TCA CAA ATA GAG      949
Pro Val Ser Ile Phe Lys Val Leu Tyr Ser Val Phe Ser Gln Ile Glu
240                 245                 250                 255

AAG ACT AAT ATT GCA GAC CTG GTG ACA GCT CTG ATT GTC CTT TTG GTT      997
Lys Thr Asn Ile Ala Asp Leu Val Thr Ala Leu Ile Val Leu Leu Val
                260                 265                 270

GTA TCC ATT GTT AAA GAA ATA AAT CAG CGC TTC AAA GAC AAA CTT CCA     1045
Val Ser Ile Val Lys Glu Ile Asn Gln Arg Phe Lys Asp Lys Leu Pro
            275                 280                 285

GTG CCC ATT CCA ATC GAA TTC ATT ATG ACC GTG ATT GCA GCA GGT GTA     1093
Val Pro Ile Pro Ile Glu Phe Ile Met Thr Val Ile Ala Ala Gly Val
        290                 295                 300

TCC TAC GGC TGT GAC TTT AAA AAC AGG TTT AAA GTG GCT GTG GTT GGG     1141
Ser Tyr Gly Cys Asp Phe Lys Asn Arg Phe Lys Val Ala Val Val Gly
    305                 310                 315

GAC ATG AAT CCT GGA TTT CAG CCC CCT ATT ACA CCT GAC GTG GAG ACT     1189
Asp Met Asn Pro Gly Phe Gln Pro Pro Ile Thr Pro Asp Val Glu Thr
320                 325                 330                 335

TTC CAA AAC ACC GTA GGA GAT TGC TTC GGC ATC GCA ATG GTT GCA TTT     1237
Phe Gln Asn Thr Val Gly Asp Cys Phe Gly Ile Ala Met Val Ala Phe
                340                 345                 350

GCA GTG GCC TTT TCA GTT GCC AGC GTC TAT TCC CTC AAA TAC GAT TAT     1285
Ala Val Ala Phe Ser Val Ala Ser Val Tyr Ser Leu Lys Tyr Asp Tyr
            355                 360                 365

CCA CTT GAT GGC AAT CAG GAG TTA ATA GCC TTG GGA CTG GGT AAC ATA     1333
Pro Leu Asp Gly Asn Gln Glu Leu Ile Ala Leu Gly Leu Gly Asn Ile
        370                 375                 380

GTC TGT GGA GTA TTC AGA GGA TTT GCT GGG AGT ACT GCC CTC TCC AGA     1381
Val Cys Gly Val Phe Arg Gly Phe Ala Gly Ser Thr Ala Leu Ser Arg
    385                 390                 395

TCA GCA GTT CAG GAG AGC ACA GGA GGC AAA ACA CAG ATT GCT GGG CTT     1429
Ser Ala Val Gln Glu Ser Thr Gly Gly Lys Thr Gln Ile Ala Gly Leu
400                 405                 410                 415

ATT GGT GCC ATC ATC GTG CTG ATT GTC GTT CTA GCC ATT GGA TTT CTC     1477
Ile Gly Ala Ile Ile Val Leu Ile Val Val Leu Ala Ile Gly Phe Leu
                420                 425                 430
```

```
CTG GCG CCT CTA CAA AAG TCC GTC CTG GCA GCT TTA GCA TTG GGA AAC    1525
Leu Ala Pro Leu Gln Lys Ser Val Leu Ala Ala Leu Ala Leu Gly Asn
            435                 440                 445

TTA AAG GGA ATG CTG ATG CAG TTT GCT GAA ATA GGC AGA TTG TGG CGA    1573
Leu Lys Gly Met Leu Met Gln Phe Ala Glu Ile Gly Arg Leu Trp Arg
            450                 455                 460

AAG GAC AAA TAT GAT TGT TTA ATT TGG ATC ATG ACC TTC ATC TTC ACC    1621
Lys Asp Lys Tyr Asp Cys Leu Ile Trp Ile Met Thr Phe Ile Phe Thr
            465                 470                 475

ATT GTC CTG GGA CTC GGG TTA GGC CTG GCA GCT AGT GTG GCA TTT CAA    1669
Ile Val Leu Gly Leu Gly Leu Gly Leu Ala Ala Ser Val Ala Phe Gln
480                 485                 490                 495

CTG CTA ACC ATC GTG TTC AGG ACC CAA TTT CCA AAA TGC AGC ACG CTG    1717
Leu Leu Thr Ile Val Phe Arg Thr Gln Phe Pro Lys Cys Ser Thr Leu
            500                 505                 510

GCT AAT ATT GGA AGA ACC AAC ATC TAT AAG AAT AAA AAA GAT TAT TAT    1765
Ala Asn Ile Gly Arg Thr Asn Ile Tyr Lys Asn Lys Lys Asp Tyr Tyr
            515                 520                 525

GAT ATG TAT GAG CCA GAA GGA GTG AAA ATT TTC AGA TGT CCA TCT CCT    1813
Asp Met Tyr Glu Pro Glu Gly Val Lys Ile Phe Arg Cys Pro Ser Pro
            530                 535                 540

ATC TAC TTT GCA AAC ATT GGT TTC TTT AGG CGG AAA CTT ATC GAT GCT    1861
Ile Tyr Phe Ala Asn Ile Gly Phe Phe Arg Arg Lys Leu Ile Asp Ala
        545                 550                 555

GTT GGC TTT AGT CCA CTT CGA ATT CTA CGC AAG CGC AAC AAA GCT TTG    1909
Val Gly Phe Ser Pro Leu Arg Ile Leu Arg Lys Arg Asn Lys Ala Leu
560                 565                 570                 575

AGG AAA ATC CGA AAA CTG CAG AAG CAA GGC TTG CTA CAA GTG ACA CCA    1957
Arg Lys Ile Arg Lys Leu Gln Lys Gln Gly Leu Leu Gln Val Thr Pro
            580                 585                 590

AAA GGA TTT ATA TGT ACT GTT GAC ACC ATA AAA GAT TCT GAC GAA GAG    2005
Lys Gly Phe Ile Cys Thr Val Asp Thr Ile Lys Asp Ser Asp Glu Glu
            595                 600                 605

CTG GAC AAC AAT CAG ATA GAA GTA CTG GAC CAG CCA ATC AAT ACC ACA    2053
Leu Asp Asn Asn Gln Ile Glu Val Leu Asp Gln Pro Ile Asn Thr Thr
            610                 615                 620

GAC CTG CCT TTC CAC ATT GAC TGG AAT GAT GAT CTT CCT CTC AAC ATT    2101
Asp Leu Pro Phe His Ile Asp Trp Asn Asp Asp Leu Pro Leu Asn Ile
            625                 630                 635

GAG GTC CCC AAA ATC AGC CTC CAC AGC CTC ATT CTC GAC TTT TCA GCA    2149
Glu Val Pro Lys Ile Ser Leu His Ser Leu Ile Leu Asp Phe Ser Ala
640                 645                 650                 655

GTG TCC TTT CTT GAT GTT TCT TCA GTG AGG GGC CTT AAA TCG ATT TTG    2197
Val Ser Phe Leu Asp Val Ser Ser Val Arg Gly Leu Lys Ser Ile Leu
            660                 665                 670

CAA GAA TTT ATC AGG ATC AAG GTA GAT GTG TAT ATC GTT GGA ACT GAT    2245
Gln Glu Phe Ile Arg Ile Lys Val Asp Val Tyr Ile Val Gly Thr Asp
            675                 680                 685

GAT GAC TTC ATT GAG AAG CTT AAC CGG TAT GAA TTT TTT GAT GGT GAA    2293
Asp Asp Phe Ile Glu Lys Leu Asn Arg Tyr Glu Phe Phe Asp Gly Glu
            690                 695                 700

GTG AAA AGC TCA ATA TTT TTC TTA ACA TCA TGA TGC TGT TTG CAT        2341
Val Lys Ser Ser Ile Phe Phe Leu Thr Ile His Asp Ala Val Leu His
            705                 710                 715

ATT TTG ATG AAG AAA GAT TAC AGT ACT TCA AAG TTT AAT CCC AGT CAG    2389
Ile Leu Met Lys Lys Asp Tyr Ser Thr Ser Lys Phe Asn Pro Ser Gln
720                 725                 730                 735

GAA AAA GAT GGA AAA ATT GAT TTT ACC ATA AAT ACA AAT GGA GGA TTA    2437
Glu Lys Asp Gly Lys Ile Asp Phe Thr Ile Asn Thr Asn Gly Gly Leu
```

```
                    740             745              750
CGT AAT CGG GTA TAT GAG GTG CCA GTT GAA ACA AAA TTC TAATCAACAT        2486
Arg Asn Arg Val Tyr Glu Val Pro Val Glu Thr Lys Phe
            755             760              765

ATAATTCAGA AGGATCTTCA TCTGACTATG ACATAAAAAC AACTTTATAC CCAGAAAGTT    2546

ATTGATAAGT TCATACATTG TACGAAGAGT ATTTTTGACA GAATATGTTT CAAACTTTGG    2606

AACAAGATGG TTCTAGCATG GCATATTTTT CACATATCTA GTATGAAATT ATATAAGTAT    2666

TCTAAATTTT ATATCTTGTA GCTTTATCAA AGGGTGAAAA TTATTTTGTT CATACATATT    2726

TTTGTAGCAC TGACAGATTT CCATCCTAGT CACTACCTTC ATGCATAGGT TTAGCAGTAT    2786

AGTGGCGCCA CTGTTTTGAA TCTCATAATT TATACAGGTC ATATTAATAT ATTTCCATTA    2846

AAAAATCAGT TGTACAGTNG AAAAAAAAAA AGAAAA                              2882

(2) INFORMATION FOR SEQ ID NO:2:

(i) SEQUENCE CHARACTERISTICS:
        (A) LENGTH: 764 amino acids
        (B) TYPE: amino acid
        (D) TOPOLOGY: linear (ii) MOLECULE TYPE: protein (xi) SEQUENCE DESCRIPTION: SEQ ID NO:2:

Met Ile Glu Pro Phe Gly Asn Gln Tyr Ile Val Ala Arg Pro Val Tyr
  1               5                  10                  15

Ser Thr Asn Ala Phe Glu Glu Asn His Lys Lys Thr Gly Arg His His
             20                  25                  30

Lys Thr Phe Leu Asp His Leu Lys Val Cys Cys Ser Cys Ser Pro Gln
         35                  40                  45

Lys Ala Lys Arg Ile Val Leu Ser Leu Phe Pro Ile Ala Ser Trp Leu
     50                  55                  60

Pro Ala Tyr Arg Leu Lys Glu Trp Leu Leu Ser Asp Ile Val Ser Gly
 65                  70                  75                  80

Ile Ser Thr Gly Ile Val Ala Val Leu Gln Gly Leu Ala Phe Ala Leu
                 85                  90                  95

Leu Val Asp Ile Pro Pro Val Tyr Gly Leu Tyr Ala Ser Phe Phe Pro
            100                 105                 110

Ala Ile Ile Tyr Leu Phe Phe Gly Thr Ser Arg His Ile Ser Val Gly
        115                 120                 125

Pro Phe Pro Ile Leu Ser Met Met Val Gly Leu Ala Val Ser Gly Ala
    130                 135                 140

Val Ser Lys Ala Val Pro Asp Arg Asn Ala Thr Thr Leu Gly Leu Pro
145                 150                 155                 160

Asn Asn Ser Asn Asn Ser Ser Leu Leu Asp Asp Glu Arg Val Arg Val
                165                 170                 175

Ala Ala Ala Ala Ser Val Thr Val Leu Ser Gly Ile Ile Gln Leu Ala
            180                 185                 190

Phe Gly Ile Leu Arg Ile Gly Phe Val Val Ile Tyr Leu Ser Glu Ser
        195                 200                 205

Leu Ile Ser Gly Phe Thr Thr Ala Ala Ala Val His Val Leu Val Ser
    210                 215                 220

Gln Leu Lys Phe Ile Phe Gln Leu Thr Val Pro Ser His Thr Asp Pro
225                 230                 235                 240

Val Ser Ile Phe Lys Val Leu Tyr Ser Val Phe Ser Gln Ile Glu Lys
                245                 250                 255
```

-continued

Thr Asn Ile Ala Asp Leu Val Thr Ala Leu Ile Val Leu Leu Val Val
            260                 265                 270

Ser Ile Val Lys Glu Ile Asn Gln Arg Phe Lys Asp Lys Leu Pro Val
        275                 280                 285

Pro Ile Pro Ile Glu Phe Ile Met Thr Val Ile Ala Ala Gly Val Ser
        290                 295                 300

Tyr Gly Cys Asp Phe Lys Asn Arg Phe Lys Val Ala Val Val Gly Asp
305                 310                 315                 320

Met Asn Pro Gly Phe Gln Pro Pro Ile Thr Pro Asp Val Glu Thr Phe
                325                 330                 335

Gln Asn Thr Val Gly Asp Cys Phe Gly Ile Ala Met Val Ala Phe Ala
            340                 345                 350

Val Ala Phe Ser Val Ala Ser Val Tyr Ser Leu Lys Tyr Asp Tyr Pro
            355                 360                 365

Leu Asp Gly Asn Gln Glu Leu Ile Ala Leu Gly Leu Gly Asn Ile Val
        370                 375                 380

Cys Gly Val Phe Arg Gly Phe Ala Gly Ser Thr Ala Leu Ser Arg Ser
385                 390                 395                 400

Ala Val Gln Glu Ser Thr Gly Gly Lys Thr Gln Ile Ala Gly Leu Ile
                405                 410                 415

Gly Ala Ile Ile Val Leu Ile Val Val Leu Ala Ile Gly Phe Leu Leu
                420                 425                 430

Ala Pro Leu Gln Lys Ser Val Leu Ala Ala Leu Ala Leu Gly Asn Leu
            435                 440                 445

Lys Gly Met Leu Met Gln Phe Ala Glu Ile Gly Arg Leu Trp Arg Lys
        450                 455                 460

Asp Lys Tyr Asp Cys Leu Ile Trp Ile Met Thr Phe Ile Phe Thr Ile
465                 470                 475                 480

Val Leu Gly Leu Gly Leu Gly Leu Ala Ala Ser Val Ala Phe Gln Leu
                485                 490                 495

Leu Thr Ile Val Phe Arg Thr Gln Phe Pro Lys Cys Ser Thr Leu Ala
            500                 505                 510

Asn Ile Gly Arg Thr Asn Ile Tyr Lys Asn Lys Lys Asp Tyr Tyr Asp
            515                 520                 525

Met Tyr Glu Pro Glu Gly Val Lys Ile Phe Arg Cys Pro Ser Pro Ile
        530                 535                 540

Tyr Phe Ala Asn Ile Gly Phe Phe Arg Arg Lys Leu Ile Asp Ala Val
545                 550                 555                 560

Gly Phe Ser Pro Leu Arg Ile Leu Arg Lys Asn Lys Ala Leu Arg
                565                 570                 575

Lys Ile Arg Lys Leu Gln Lys Gln Gly Leu Leu Gln Val Thr Pro Lys
            580                 585                 590

Gly Phe Ile Cys Thr Val Asp Thr Ile Lys Asp Ser Asp Glu Glu Leu
        595                 600                 605

Asp Asn Asn Gln Ile Glu Val Leu Asp Gln Pro Ile Asn Thr Thr Asp
610                 615                 620

Leu Pro Phe His Ile Asp Trp Asn Asp Leu Pro Leu Asn Ile Glu
625                 630                 635                 640

Val Pro Lys Ile Ser Leu His Ser Leu Ile Leu Asp Phe Ser Ala Val
                645                 650                 655

Ser Phe Leu Asp Val Ser Ser Val Arg Gly Leu Lys Ser Ile Leu Gln
            660                 665                 670

```
Glu Phe Ile Arg Ile Lys Val Asp Val Tyr Ile Val Gly Thr Asp Asp
            675                 680                 685

Asp Phe Ile Glu Lys Leu Asn Arg Tyr Glu Phe Phe Asp Gly Glu Val
        690                 695                 700

Lys Ser Ser Ile Phe Phe Leu Thr Ile His Asp Ala Val Leu His Ile
705                 710                 715                 720

Leu Met Lys Lys Asp Tyr Ser Thr Ser Lys Phe Asn Pro Ser Gln Glu
                725                 730                 735

Lys Asp Gly Lys Ile Asp Phe Thr Ile Asn Thr Asn Gly Gly Leu Arg
            740                 745                 750

Asn Arg Val Tyr Glu Val Pro Val Glu Thr Lys Phe
            755                 760
```

(2) INFORMATION FOR SEQ ID NO:3:

(i) SEQUENCE CHARACTERISTICS:
        (A) LENGTH: 8 amino acids
        (B) TYPE: amino acid
        (D) TOPOLOGY: linear (xi) SEQUENCE DESCRIPTION: SEQ ID NO:3:

```
Arg Trp Gly Lys Arg Lys Asn Lys
1               5
```

(2) INFORMATION FOR SEQ ID NO:4:

(i) SEQUENCE CHARACTERISTICS:
        (A) LENGTH: 8 amino acids
        (B) TYPE: amino acid
        (D) TOPOLOGY: linear (xi) SEQUENCE DESCRIPTION: SEQ ID NO:4:

```
Gly Gly Pro Lys Lys Lys Arg Lys
1               5
```

(2) INFORMATION FOR SEQ ID NO:5:

(i) SEQUENCE CHARACTERISTICS:
        (A) LENGTH: 22 amino acids
        (B) TYPE: amino acid
        (D) TOPOLOGY: linear (xi) SEQUENCE DESCRIPTION: SEQ ID NO:5:

```
Leu Asp Gly Glu Asp Val Ala Met Ala His Ala Asp Ala Leu Asp Asp
1               5                   10                  15

Phe Asp Leu Asp Met Leu
            20
```

(2) INFORMATION FOR SEQ ID NO:6:

(i) SEQUENCE CHARACTERISTICS:
        (A) LENGTH: 22 amino acids
        (B) TYPE: amino acid
        (D) TOPOLOGY: linear (xi) SEQUENCE DESCRIPTION: SEQ ID NO:6:

```
Leu Gln Asn Gln Gln Val Leu Thr Gly Leu Pro Gly Val Met Pro Asn
1               5                   10                  15

Ile Gln Tyr Gln Val Ile
            20
```

(2) INFORMATION FOR SEQ ID NO:7:

```
        (i) SEQUENCE CHARACTERISTICS:
             (A) LENGTH: 22 amino acids
             (B) TYPE: amino acid
             (D) TOPOLOGY: linear (xi) SEQUENCE DESCRIPTION: SEQ ID NO:7:

Ile Arg Thr Pro Thr Val Gly Pro Asn Gly Gln Val Ser Trp Gln Thr
1               5                   10                  15

Leu Gln Leu Gln Asn Leu
            20

(2) INFORMATION FOR SEQ ID NO:8:

(i) SEQUENCE CHARACTERISTICS:
             (A) LENGTH: 5 amino acids
             (B) TYPE: amino acid
             (D) TOPOLOGY: linear (ix) FEATURE:
             (A) NAME/KEY: Peptide
             (B) LOCATION: 1
             (D) OTHER INFORMATION: /note= "Xaa at position 1 can be
                 Arg, Lys, Thr, or Ala"

(ix) FEATURE:
             (A) NAME/KEY: Peptide
             (B) LOCATION: 4
             (D) OTHER INFORMATION: /note= "Xaa at position 4 can be
                 Arg, Gln, Asn, Thr, Ser or Gly"

(xi) SEQUENCE DESCRIPTION: SEQ ID NO:8:

Xaa Lys Lys Xaa Lys
1               5
```